US007753226B2

(12) United States Patent
Chauvin

(10) Patent No.: US 7,753,226 B2
(45) Date of Patent: Jul. 13, 2010

(54) ORAL MEDICINE DISPENSER

(76) Inventor: Marc Chauvin, 23106 Enchanted Landing La., Katy, TX (US) 77494

( * ) Notice: Subject to any disclaimer, the term of this patent is extended or adjusted under 35 U.S.C. 154(b) by 1209 days.

(21) Appl. No.: 11/248,678

(22) Filed: Oct. 13, 2005

(65) Prior Publication Data

US 2007/0088251 A1 Apr. 19, 2007

(51) Int. Cl.
*A47G 19/22* (2006.01)
*B65D 41/04* (2006.01)
*A61N 1/30* (2006.01)

(52) U.S. Cl. ....................... 220/714; 220/705; 220/288; 604/19

(58) Field of Classification Search ................ D24/121; 220/694, 703, 702; 604/19, 403; 215/229, 215/388
See application file for complete search history.

(56) References Cited

U.S. PATENT DOCUMENTS

D290,323 S 6/1987 Weernink
D310,567 S 9/1990 Fitzpatrick
D343,451 S * 1/1994 Voychehovski ............ D24/121
D359,417 S 6/1995 Chen
D359,882 S 7/1995 Birge, Jr.
D361,469 S 8/1995 Young
D363,852 S 11/1995 Young
D390,785 S 2/1998 Saunders et al.
D407,269 S 3/1999 Fletcher
5,890,620 A * 4/1999 Belcastro .................... 220/714
5,890,621 A * 4/1999 Bachman et al. ............ 220/717
5,988,425 A * 11/1999 Yehl et al. ................... 220/303
D419,029 S 1/2000 Randolph
D435,906 S 1/2001 Wilkinson
6,179,146 B1 * 1/2001 Betras ........................ 220/23.4
6,230,923 B1 * 5/2001 Hung ......................... 220/703
D444,874 S 7/2001 Haffner et al.
6,755,318 B2 * 6/2004 Burke et al. ................ 220/703
6,758,364 B1 * 7/2004 Rohrig ....................... 220/714
6,877,626 B2 * 4/2005 Sherrod ...................... 215/319
6,883,677 B2 * 4/2005 Goeking et al. ............. 220/713
6,976,604 B2 * 12/2005 Connors et al. ............. 220/713
D528,860 S 9/2006 McGrath
D546,626 S 7/2007 Chou
D559,622 S 1/2008 Carreno
7,318,536 B2 * 1/2008 Maravich et al. ............ 220/780
7,402,092 B1 * 7/2008 Randall et al. ................ 446/74
D574,488 S 8/2008 Chauvin
2001/0027956 A1 * 10/2001 Bonacorso et al. ......... 215/11.1
2003/0192891 A1 10/2003 Ziegler
2004/0045928 A1 * 3/2004 Lepage ....................... 215/388
2005/0247719 A1 * 11/2005 Loging ....................... 220/714
2005/0284302 A1 * 12/2005 Levin .......................... 99/275
2006/0006184 A1 * 1/2006 Bohman et al. ............. 220/717
2006/0060552 A1 * 3/2006 Kasprzak ................... 215/11.1
2008/0283537 A1 * 11/2008 Smith et al. ................. 220/713

* cited by examiner

*Primary Examiner*—Nicholas D Lucchesi
*Assistant Examiner*—Victoria P Campbell
(74) *Attorney, Agent, or Firm*—Arnold & Knobloch, L.L.P.; Charles Knobloch

(57) ABSTRACT

An oral medicine dispenser for administering liquid medicine to a child includes: a cup having a cap and nozzle with a medicine compartment located therein. When a child sucks the nozzle, the medicine flows from the medicine container into the nozzle. The nozzle has two separate chambers. One chamber of the nozzle delivers the medicine from the medicine compartment to the back of the child's mouth. The other chamber delivers a fluid such as juice from the cup to the front of the child's mouth so as to taste more appealing to the child.

6 Claims, 3 Drawing Sheets

ORAL MEDICINE DISPENSER

BACKGROUND OF THE INVENTION

Field of the Invention

This invention concerns an oral medicine dispenser for administering liquid medicine to young children that effectively hides the taste of the medicine by delivering the medicine to the back of the throat to avoid the taste buds while delivering a fluid, such as juice, towards the front of the mouth to cover the taste buds.

SUMMARY OF THE INVENTION

Accordingly, it is an object of the invention to provide an oral medicine dispenser for administering liquid medicine to young children that effectively hides the taste of the medicine.

In order to achieve the above and other objects of the invention, an oral medicine dispenser includes, according to a first aspect of the invention, a cup for holding fluid having a threaded neck portion at the upper end thereof that defines an opening therein; a cap having threads in the interior portion of the cap that mate with the threads of the cup; a conduit for entry of air into the cup having an aperture in the cap for entry of air into the conduit and the cup; a medicine compartment located in the cap for holding liquid medicine; a conduit for entry of air through an aperture in the cap into the medicine compartment and a value to regulate the passage of air into the medicine compartment; a nozzle projecting from the cap with a divider forming a chamber to carry the medicine exiting the medicine compartment and a second chamber to carry the fluid exiting the cup to prevent mixing before exiting the nozzle; a valve for regulating the flow of medicine from the medicine compartment to the first chamber of the nozzle, and a removable flexible member adapted for sealing the medicine compartment, the conduit for entry of air into the cup and the chambers of the nozzle and having a valve for controlling air flow into the cup and another valve for controlling fluid exiting the cup into the second chamber of the nozzle.

According to another aspect of the invention, the removable flexible member includes a plug adapted to close the conduit to prevent air from passing through the aperture in the cap into the medicine compartment so as to allow a child to use the invention as a cup with a lid having a spout for delivery of fluid, such as juice, without an oral medicine.

These and various other advantages and features of novelty which characterize the invention are pointed out with particularity in the claims annexed thereto and forming a part hereof. However, for a better understanding of the invention, its advantages, and the objects obtained by its use, reference should be made to the drawings which form a further part hereof, and to the accompanying descriptive matter, in which there is illustrated and described a preferred embodiment of the invention.

DETAILED DESCRIPTION OF PREFERRED EMBODIMENT

Figure 1:
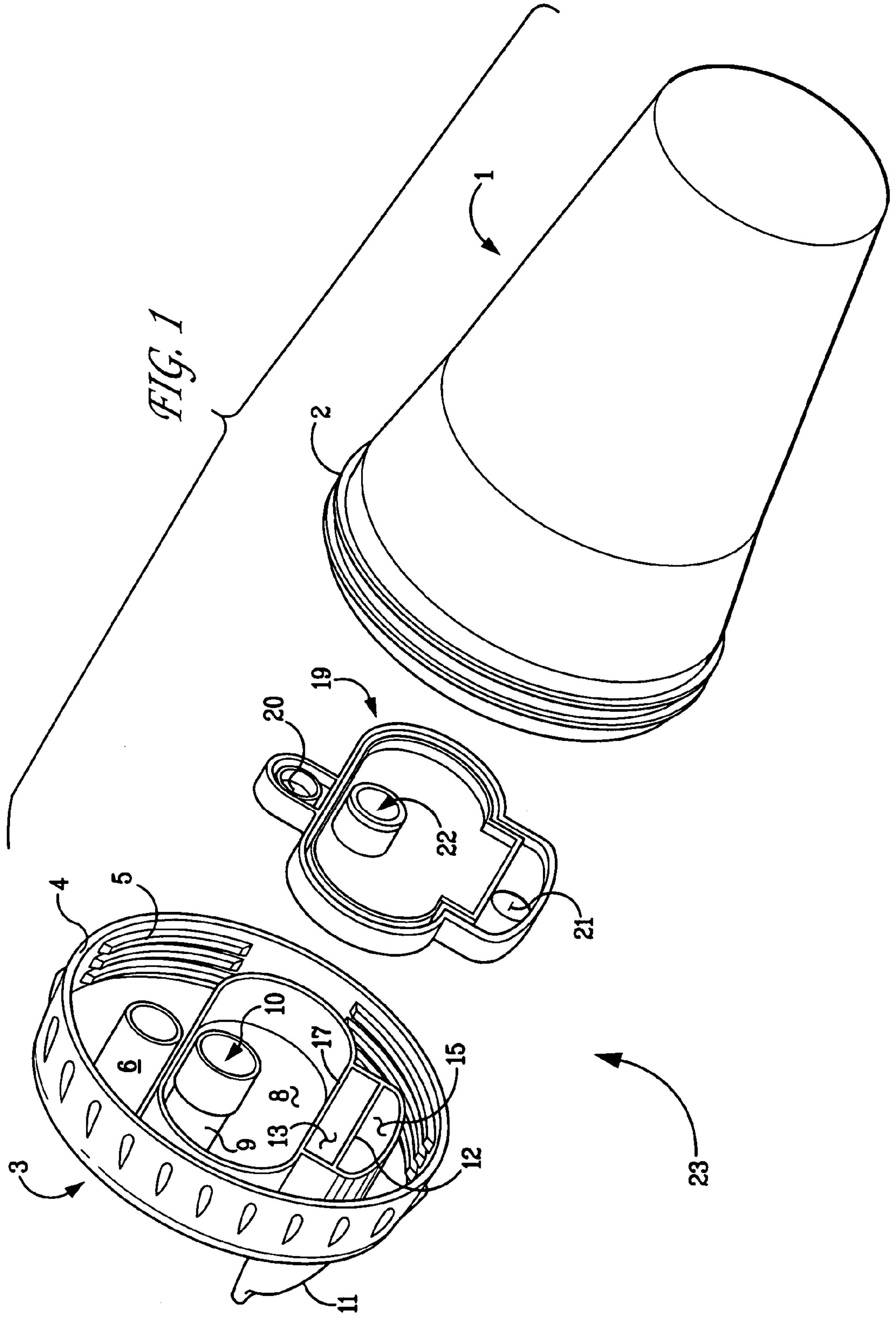
FIG. 1 is an exploded-perspective view of the present invention illustrating an oral liquid medicine dispenser.

Referring to FIG. 1, an oral medicine dispenser 23 for administering liquid medicine to a young child includes a cup 1 for holding fluid such as juice or milk, a cap 3 having a nozzle 11 for a child to suck, and a medicine compartment 8 inside the cap 3 for delivering medicine to the child. The dispenser 23 can be manufactured as one piece of molded plastic.

The cup 1 has a threaded portion 2 at the upper end thereof near the opening of the cup 1 that is mated to the threads 5 on the rim 4 inside of the cap 3.

Figure 2:
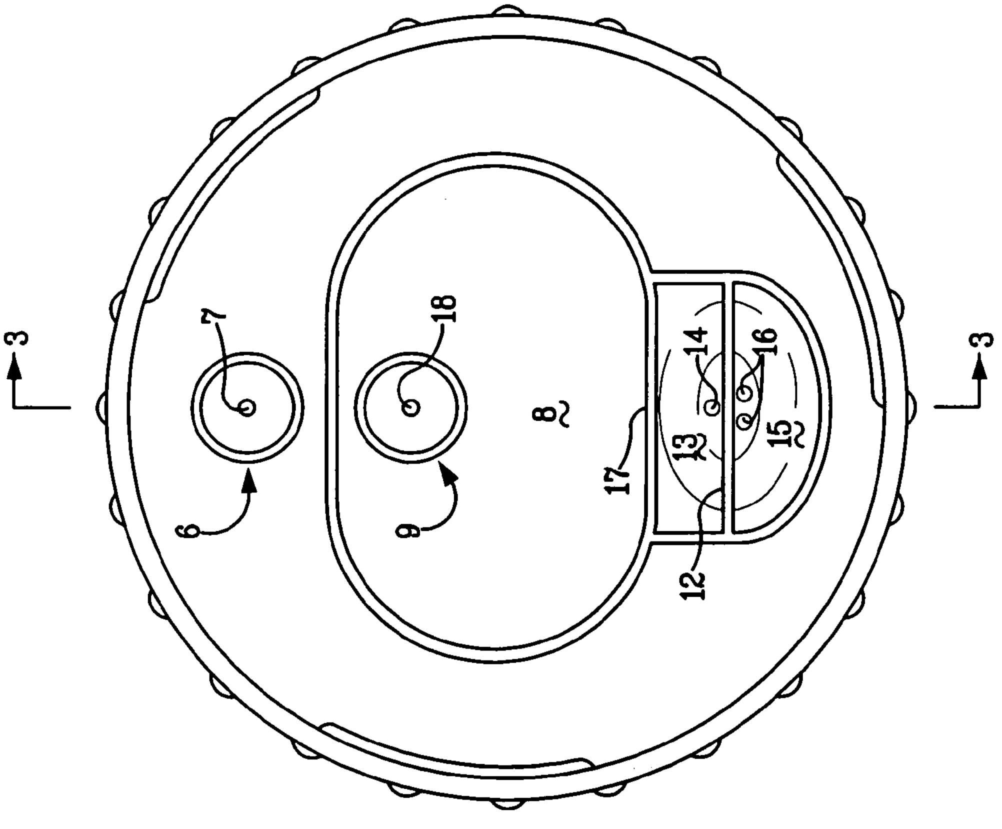
FIG. 2 is an enlarged view of the inside of the cap of the dispenser of FIG. 1.

The cap 3 has an aperture 7 shown in FIG. 2 for air to enter conduit 6 into the cup 1. Additionally, the cap 3 has another aperture 18 for air to enter conduit 9 into the medicine compartment 8. Valve 10 shown in FIG. 1 regulates the air passing through conduit 9 into the medicine compartment 8.

The nozzle 11 shown in FIG. 1 is partitioned into two separate chambers as shown in FIG. 2 by a divider 12. Medicine exits the medicine compartment 8 through valve 17 which controls the rate of medicine entering the first chamber 13 of the nozzle 11. The second chamber 15 delivers fluid such as juice or milk from the cup 1. When a child sucks on the nozzle 11 medicine and fluid exit the nozzle 11 through openings 14 and 16. The medicine and fluid do not mix prior to exiting the nozzle.

Figure 3:
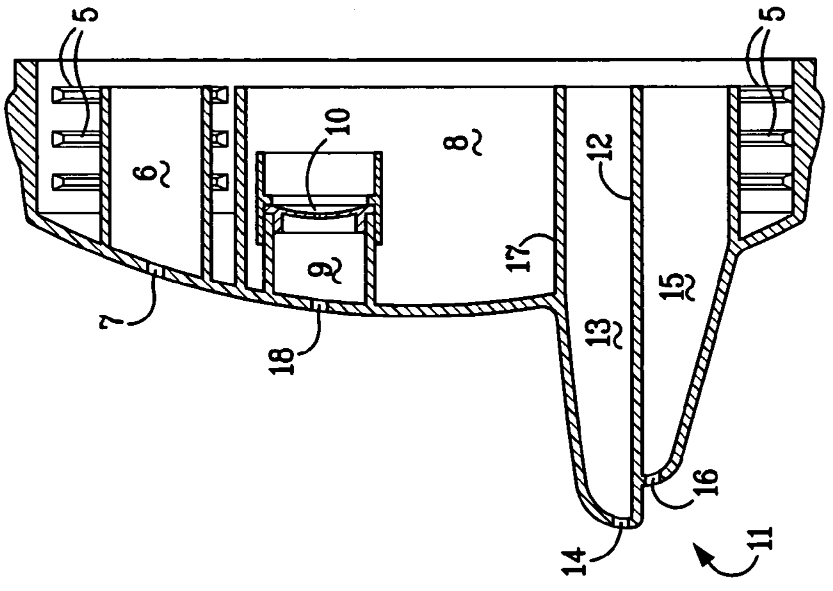
FIG. 3 is an enlarged side view illustrating the cap of the dispenser of FIG. 1.

In a preferred embodiment of the invention, the first chamber 13 is longer than the second chamber 15 shown in FIG. 3. When the child sucks on the nozzle 11, the medicine exits the nozzle 11 in the back of the child's mouth to avoid the taste buds whereas the fluid exits the nozzle 11 towards the front of the child's mouth to cover the taste buds first. In another preferred embodiment of the invention, the opening 14 at the tip of the nozzle 11 for carrying the medicine in the first chamber 13 is smaller than the opening 16 at the tip of the nozzle 11 for carrying the fluid in the second chamber 15. The openings 14 and 16 may be single apertures or a plurality of apertures. By delivering the medicine at a slower rate than the fluid, the child is less likely to detect the taste of the medicine thereby making it easier to administer the medicine.

Figure 4:
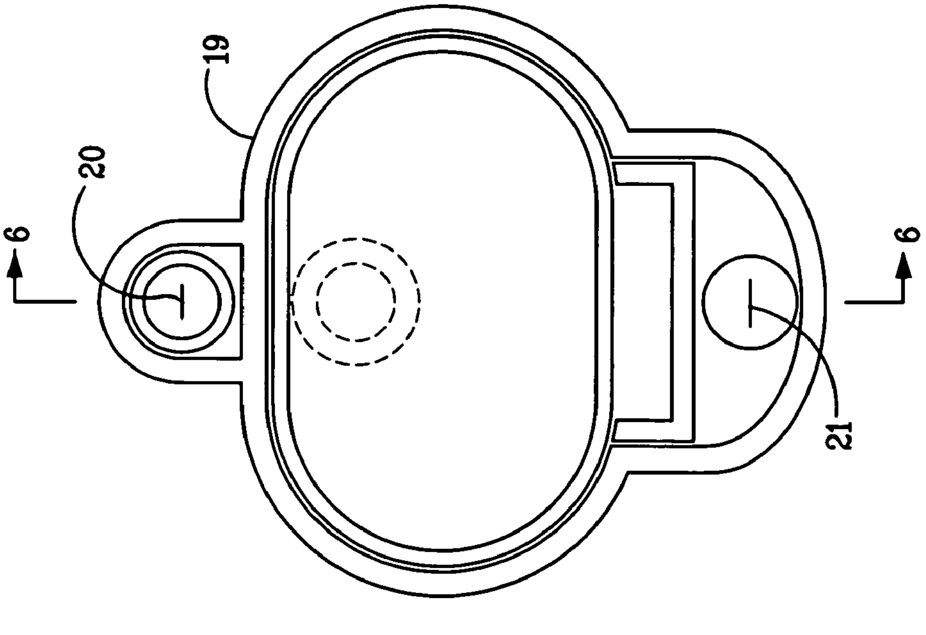
FIG. 4 is an enlarged view of the flexible member of the dispenser of FIG. 1.

Referring to FIG. 1, a removable flexible member 19 such as soft silicone rubber is adapted for sealing the medicine compartment 8 so that the medicine does not mix with the fluid in the cup 1. In operation, after medicine is placed in the medicine compartment 8, the flexible member 19 is placed on the medicine compartment 8. The flexible member 19 also seals the first conduit 6 and the first chamber 13 and second chamber 15 of the nozzle 11. A valve 20 in the flexible member 19, such as a slit, shown in FIG. 4 controls air flow through the first conduit 6 into the cup 1. A second valve 21 in the flexible member 19, such as a slit, controls the rate of fluid exiting the cup 1 into the second chamber 15 of the nozzle 11. Additionally, the second valve 21 helps to prevent fluid from leaking out of the cup 1.

Figure 6:
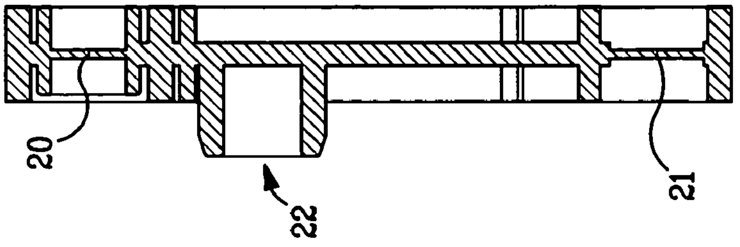
FIG. 6 is an enlarged cross-sectional view of the flexible member of the dispenser shown in FIGS. 4 and 5.
Figure 5:
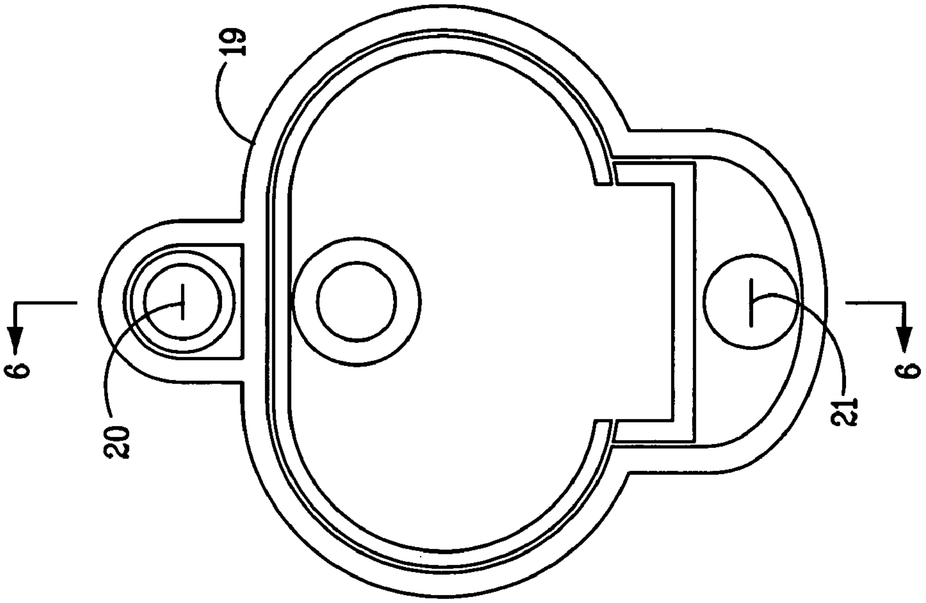
FIG. 5 is an enlarged view of the opposite side of the flexible member of the dispenser of FIG. 4 illustrating the plug.

In another preferred embodiment of the invention, the cup 1 can be used to deliver only fluid when administering medicine is not needed. FIG. 5 illustrates the opposite side of the flexible member 19 shown in FIG. 4. This side of the flexible member 19 has a plug 22 also shown in FIG. 6 that is adapted to close second conduit 9 shown in FIG. 1 to prevent air from passing through the second aperture 18 in the cap 3 into the medicine compartment 8. The plug 22 prevents the child from sucking air into the medicine compartment 8 which would eventually be swallowed by a child.

It is to be understood, however, that even though numerous characteristics and advantages of the present invention have been set forth in the foregoing description, together with details of the structure and function of the invention, the disclosure is illustrative only, and changes may be made in detail, especially in matters of shape, size and arrangement of parts within the principles of the invention to the full extent indicated by the broad general meaning of the terms in which the appended claims are expressed.

What is claimed is:

1. An oral medicine dispenser for administering liquid medicine comprising:

a cup for holding fluid, said cup having a threaded neck portion at the upper end thereof that defines an opening therein;

a cap, said cap having threads in the interior portion of said cap that mate with the threads of said cup, a first conduit for entry of air into said cup, said first conduit having a first aperture in said cap for entry of air into said first conduit and said cup, a medicine compartment located in said cap for holding liquid medicine, a second conduit for entry of air into said medicine compartment, said second conduit comprising an aperture in said cap for entry of air into said second conduit and said medicine compartment, said second conduit further comprising a value to regulate the passage of air from said second conduit into said medicine compartment, a nozzle projecting from said cap, said nozzle having a divider forming a first chamber to carry the medicine exiting said medicine compartment and a second chamber to carry the fluid exiting said cup to prevent mixing before exiting said nozzle, said nozzle having an opening for said first chamber for medicine to exit said nozzle and an opening for said second chamber for fluid to exit said nozzle, a valve for regulating the flow of medicine from said medicine compartment to said first chamber of said nozzle, and a removable flexible member adapted for sealing said medicine compartment, said first conduit and said first and second chambers of said nozzle, said member further comprising a first valve for controlling air flow through said first conduit into said cup, and a second valve for controlling fluid exiting said cup into said second chamber of said nozzle.

2. The dispenser of claim 1, including a plug adapted to close said second conduit to prevent air from passing through said second aperture in said cap into said medicine compartment.

3. The dispenser of claim 1, wherein said flexible member is manufactured from silicone.

4. The dispenser of claim 1, wherein said first and second valves of said flexible member are slits.

5. The dispenser of claim 1, wherein the first chamber of said nozzle is longer than said second chamber to dispense medicine further back in a mouth of a child to avoid the taste buds.

6. The dispenser of claim 1, wherein the opening of said nozzle for said first chamber is smaller than the opening of said nozzle for said second chamber.

* * * * *